United States Patent [19]

Moreau et al.

[11] 4,372,954
[45] Feb. 8, 1983

[54] MOROXYDINE PHENOXYISOBUTYRATES AND METHOD OF USE

[76] Inventors: Pierre D. Moreau, 61 Grande Rue, Bessancourt, France, 95550; Nils A. Jonsson, Jungfrudansen 15, Solna S-171 56, Sweden

[21] Appl. No.: 308,546
[22] PCT Filed: Feb. 5, 1981
[86] PCT No.: PCT/FR81/00012
  § 371 Date: Oct. 1, 1981
  § 102(e) Date: Oct. 1, 1981
[87] PCT Pub. No.: WO81/02295
  PCT Pub. Date: Aug. 20, 1981

[30] Foreign Application Priority Data
  Feb. 11, 1980 [FR] France .............. 80 02927
  Jan. 14, 1981 [FR] France .............. 81 00522

[51] Int. Cl.³ .................. A61K 31/535; C07D 295/14
[52] U.S. Cl. .................. 424/248.53; 424/248.56; 544/162
[58] Field of Search .................. 544/162; 424/248.53, 424/248.56

[56] References Cited
  U.S. PATENT DOCUMENTS
  4,089,957 12/1977 Jönsson .................. 424/248.56

FOREIGN PATENT DOCUMENTS
  2357875 9/1974 Fed. Rep. of Germany .
  2726392 12/1977 Fed. Rep. of Germany .
  2315917 1/1977 France .
  1494299 12/1977 United Kingdom .

Primary Examiner—Robert W. Ramsuer
Attorney, Agent, or Firm—Browdy and Neimark

[57] ABSTRACT

The moroxydine phenoxyisobutyrates of the present invention are characterized in that they correspond to the following general formula I:

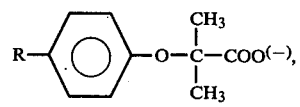

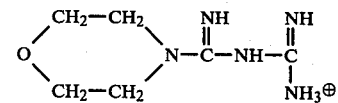

in which R represents a chlorine atom or a

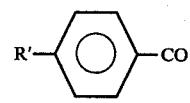

group, R' being a chlorine atom. Medicaments containing these compounds are useful for the inhibition of platelet aggregation and lowering fibrinogen.

4 Claims, No Drawings

MOROXYDINE PHENOXYISOBUTYRATES AND METHOD OF USE

FIELD OF THE INVENTION

The present invention relates to novel salts of phenoxyisobutyric acids. The pharmacological properties of the phenoxyisobutyric acids are known and notably those of p-chlorophenoxyisobutyric acid (clofibric acid) or those of its homolog, 4-(4-chloro-benzoyl)-phenoxyisobutyric acid. These acids and their derivatives) are valued for their action on the inhibition of cholesterol synthesis with a notable reduction in the cholesterol pool in the organism, on the inhibition of abnormally high blood levels of uric acid and of fibrinogen, and for their anti-atheromatous and platelet-antiaggregating actions.

However, at recognized doses, and in particular in patients whose albuminemia level is low, there is a possibility of the appearance of muscular cramps with an increase in the SGOT and the CPK. There have also been noted immuno-allergic incidents of the type of eruptions, skin rashs, leucopenia, as well as cases of biliary calculus, notably for 4-(4'-chloro-benzoyl) -phenoxyisobutyric acid. This is true for all the clofibrates and homologs at present known like aluminum clofibrate, hydroxy-aluminum clofibrate, magnesium clofibrate, ethylester of clofibric acid, isopropyl ester of 4-(4'-chloro-benzoyl)-phenoxyisobutyric acid etc. . . . Other derivatives, like, for example, metformine clofibrate, have a very pronounced hypoglycemic effect, which particularly limits the usefulness of this salt.

It is therefore an object of the present invention to provide novel derivatives of phenoxyisobutyric acids which are more active, through this reason only requiring smaller doses and consequently, not resulting in undesirable side-effects.

GENERAL DESCRIPTION OF THE INVENTION

According to the invention there are provided novel salts of phenoxyisobutyric acids constituted by moroxydine phenoxyisobutyrates of the general formula I below:

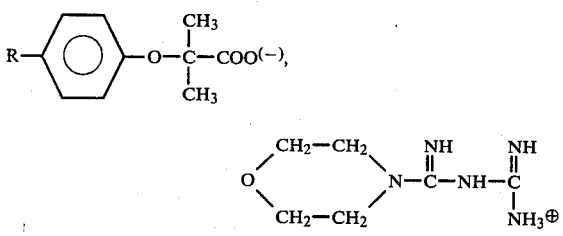

in which R represents a chlorine atom or a

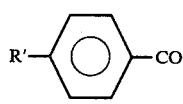

group, R' being a chlorine atom.

Moroxydine or (α-morpholine α-imino methylene)-guanidine is a known antiviral agent, which, associated, according to the invention, with clofibric or 4-(4'-chloro-benzoyl)-phenoxyisobutyric acid, potentiates surprizingly the hypolipemic properties of the latter and confers on the novel salts obtained, remarkable properties in the prevention and treatment of atheromatous and coronary manifestations and in the treatment of surface and deep veinous thromboses.

According to the invention, the moroxydine salt is prepared by reacting stoichiometric amounts of clofibric acid or of 4-(4'-chloro-benzoyl)-phenoxyisobutyric acid and moroxydine and isolating the salt obtained by crystallization.

Since moroxydine-base is difficult to handle and is not commercially available, it is preferable to start from a moroxydine salt, such as for example, moroxydine hydrochloride.

According to an advantageous embodiment of the process according to the present invention, to a clofibrate or to a 4-(4-chloro-benzoyl)-phenoxyisobutyrate is added an equimolecular amount of a moroxydine salt, in a suitable solvent medium.

According to another advantageous embodiment of the process according to the present invention, to a solution of phenoxyisobutyric acid is added an equimolecular amount of moroxydine-base obtained by passage over ion exchange resins.

Applicants have observed, to their great surprise, that moroxydine clofibrate forms a dihydrate little soluble in water below about 30° C. This product can hence easily be prepared by mixing equimolecular amounts of a hot aqueous solution of a moroxydine salt having the following composition:

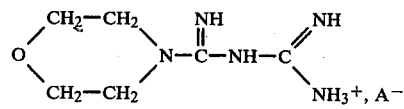

and a hot aqueous solution of a clofibric acid salt having the following composition:

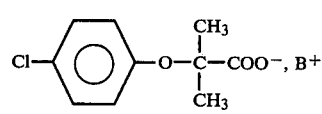

$A^-$ and $B^+$ respectively denoting an anion and a cation and being selected so that the $A^-B^+$ salt that they form is very easily soluble in water below 30° C., while the crystalline moroxydine clofibrate dihydrate is separated from the reaction mixture.

According to an advantageous embodiment of the process according to the present invention, the moroxydine clofibrate dihydrate is dried in order to obtain an anhydrous salt.

According to another advantageous embodiment of the process according to the present invention, the $A^-$ anion is selected from the group which comprises $Cl^-$, $Br^-$, $NO_3^-$, and $SO_4^{--}$, and the $B^+$ cation from the group which comprises $Na^+$, $K^+$, $NH_4^+$ and organic amines.

According to another aspect of the present invention there are also provided medicaments constituted by or containing moroxydine phenoxyisobutyrates according to the present invention.

In certain particular cases, it is desirable to break the stoichiometric equilibrium between the constituents of these medicaments, in order to provide a medicament of which the proportion of its two constituents is no longer 1:1 but, on the contrary, a medicament in which one of the constituents is in excess with respect to the other. Thus, for example, when it is desired to increase the hypolipidemic action of the medicament, it is necessary to increase the phenoxyisobutyric acid proportion.

The present invention consequently also provides medicaments containing phenoxyisobutyric acid (PBA) and moroxydine (MOR) in molecular proportions which vary from 0.10/1 to 1/0.10.

In an advantageous embodiment according to the invention, the excess phenoxyisobutyric acid is in the form of a pharmaceutically compatible inorganic and/or organic salt.

In another advantageous embodiment according to the invention, the excess moroxydine is salted by hydrochloride and/or sulfate and/or phosphate and/or carbonate and/or hydrobromide and/or nitrate ions.

Besides the foregoing features, the invention comprises other features, which will emerge from the description which follows.

DESCRIPTION OF PREFERRED EMBODIMENTS

EXAMPLES OF THE PREPARATION

Equilibrated salts

Peparation of moroxydine clofibrate (1) 430 g of clofibric acid is dissolved in 800 ml of water containing 80 g of sodium hydroxide, brought to 70° C. This solution is then added to a hot aqueous solution (about 70° C.) of 414 g of moroxydine hydrochloride in 800 ml of water. The mixture obtained was stirred for some time, then cooled to about 5° C. for 2 to 4 hours. The moroxydine clofibrate (in the form of crystalline dihydrate) is separated by filtration, washed 4 times with 300 ml of ice water each time, dried for 12 hours at room temperature, then at 80° C. to constant weight. The anhydrous product obtained weighed 644 g (84% yield) and melts at around 216° C.

| Analysis | C | H | Cl | N | O |
|---|---|---|---|---|---|
| theory | 49.8% | 6.27% | 9.19% | 18.1% | 16.8% |
| found | 49.4% | 6.17% | 9.43% | 18.2% | 16.6% | its content of NaCl was less than 0.1%.

(b 2) Potassium clofibrate was solubilized in ethanol; to this solution, in equimolecular proportions, was added an ethanol solution of moroxydine hydrochloride;

the KCl precipitate formed was removed by filtration;

the ethanol was evaporated;

the moroxydine clofibrate was crystallized in isopropyl alcohol.

Preparation of products whose constituents are not in stoichiometric proportions (1) Example of the preparation of the product containing one proportion Desired Formula: PBA/MOR=1:4

|  | MG/Day | MG/per tablet |
|---|---|---|
| Clofibric ion | 1200 | 150 |
| Moroxydine ion | 4000 | 500 |
|  | 5200 | 650 |
| Posology |  |  |
| 8 tablets per day |  |  |
| Composition |  | Grams |
| Moroxydine clofibrate 1:1 (prepared according to Example 1) |  | 270 |
| Moroxydine hydrochloride |  | 462 |
| Wheat starch |  | 100 |
| Magnesium stearate |  | 6 |

Preparation:

A granulation was prepared by mixing moroxydine clofibrate, moroxydine hydrochloride and wheat starch and by granulating their mixture by incorporating in a paste of 25 g of starch and 100 ml water. The granulate so-obtained was dried and the magnesium stearate was mixed with the dry granulate and the resulting mixture was compressed into 1000 tablets.

(2) Second Eample

Desired formula: PBA/MOR=10:1

|  | MG/day | MG/per tablet |
|---|---|---|
| Clofibric ion | 2600 | 650 |
| Moroxydine ion | 200 | 50 |
|  | 2800 | 700 |
| Posology: 4 tablets per day. |  |  |
| Composition: |  | Grams |
| Moroxydine clofibrate 1:1 (prepared according to Example 1) |  | 113 |
| Clofibric acid |  | 589 |
| Wheat starch |  | 100 |
| Magnesium Stearate |  | 6 |

Preparation

This preparation was carried out identically with that of Example 1 for 1000 tablets.

REPORT OF PHARMACOLOGICAL TESTS

Each result recorded in the following Tables corresponds to an average obtained in 15 animals. The experiments were carried out on male rats of the AF Han. EOPS WISTAR breed weighing about 250 g.

Each time the results obtained in rats treated with a product according to the invention, namely moroxydine clofibrate, were compared with those obtained by the action of clofibrate alone and of moroxydine alone.

The administration of the product was carried out orally and the amount administered was equal to 35 mg per day.

TABLE I

RATS ON HYPERLIPIDEMIC DIET
"Blood analysis"

Average values

| Products | Free Chol. mg/100ml | Chol. ester mg/l | Cholesterol of the HDL g/l | ratio HDL/ LDL + VLDL | Fibrinogen g/l | glycemia g/l | SGPT IU | urea g/l |
|---|---|---|---|---|---|---|---|---|
| Controls | 10.3 | 36.7 | 0.36 | 3.1 | 1.91 | 1.22 | 28 | 0.37 |
| Product according to the invention |  |  |  |  |  |  |  |  |

TABLE I-continued

RATS ON HYPERLIPIDEMIC DIET
"Blood analysis"

| Products | | Free Chol. mg/100ml | Chol. ester mg/l | Cholesterol of the HDL g/l | ratio HDL/ LDL + VLDL | Fibrinogen g/l | glycemia g/l | SGPT IU | urea g/l |
|---|---|---|---|---|---|---|---|---|---|
| Phenoxyisobutyric acid / Moroxydine | = 1/1 | 8.4 | 25.8 | 0.30 | 2.4 | 1.47 | 1.24 | 30 | 0.38 |
| Phenoxyisobutyric acid / Moroxydine | = 10/1 | 9.2 | 34.1 | 0.35 | 3 | 1.85 | 1.22 | 45 | 0.52 |
| Phenoxyisobutyric acid / Moroxydine | = 8/1 | 6.0 | 22.0 | 0.29 | 2.2 | 1.70 | 1.40 | 32 | 0.50 |
| Phenoxyisobutyric acid / Moroxydine | = 1/4 | 7.9 | 31.- | 0.37 | 3.3 | 1.95 | 1.20 | 27 | 0.35 |
| Clofibrate alone | | 6.4 | 22.2 | 0.29 | 2.2 | 1.59 | 1.43 | 32.5 | 0.44 |
| Moroxydine alone | | 7.9 | 32.1 | 0.38 | 3.3 | 1.99 | 1.20 | 27.1 | 0.36 |

TABLE II

RATS ON HYPERLIPIDEMIC DIET

| Products | | Free Chol. mg/100ml | Chol. ester mg/l | Cholesterol of the HDL g/l | HDL/ LDL + VLDL | SGPT IU | fibrinogen g/l | urea g/l |
|---|---|---|---|---|---|---|---|---|
| Controls | | 19.65 | 28.24 | 0.23 | 2.1 | 126.4 | 2.16 | 0.28 |
| Product according to the invention | | | | | | | | |
| Phenoxyisobutyric acid / Moroxydine | = 1/1 | 11.32 | 21.79 | 0.25 | 1.62 | 188.1 | 1.96 | 0.29 |
| Phenoxyisobutyric acid / Moroxydine | = 10/1 | 17.2 | 26.7 | 0.27 | 0.65 | 420.- | 2.19 | 0.50 |
| Phenoxyisobutyric acid / Moroxydine | = 8/1 | 10.57 | 21.71 | 0.39 | 0.77 | 302.- | 2.10 | 0.30 |
| Phenoxyisobutyric acid / Moroxydine | = 1/4 | 17.6 | 29.5 | 0.25 | 0.90 | 340.- | 1.92 | 0.26 |
| Clofibrate alone | | 10.57 | 21.7 | 0.38 | 0.773 | 302.1 | 2.2 | 0.26 |
| Moroxydine alone | | 17.5 | 29.3 | 0.25 | 0.867 | 349.9 | 1.80 | 0.30 |

TABLE III

RABBITS SEQUENTIAL DIET

| Products | | End of 2nd month | | End of 5th month | | | | | |
|---|---|---|---|---|---|---|---|---|---|
| | | Triglycer. | Cholesterol of the HDL | Fibrinogen | Total Choles. | Triglycer. | Cholesterol of the HDL | Glycemia | Urea |
| Controls | | 1.07 | 0.32 | 3.84 | 0.73 | 1.36 | 0.22 | 1.28 | 0.32 |
| Product according to the invention | | | | | | | | | |
| Phenoxyisobutyric acid / Moroxydine | = 1/1 | 0.82 | 0.36 | 2.06 | 0.66 | 0.86 | 0.17 | 1.18 | 0.33 |
| Phenoxyisobutyric acid / Moroxydine | = 10/1 | 1.12 | 0.32 | 3.54 | 0.72 | 1.34 | 0.17 | 1.28 | 0.42 |
| Phenoxyisobutyric acid / Moroxydine | = 8/1 | 0.90 | 0.30 | 2.78 | 0.65 | 1.24 | 0.17 | 1.40 | 0.40 |
| Phenoxyisobutyric acid / Moroxydine | = 1/4 | 1.25 | 0.35 | 2.90 | 0.60 | 1.35 | 0.16 | 1.35 | 0.33 |

TABLE IV

Rats in normal diet
Comparison of platelet aggregation (ADP method)

| | Velocity in % at | | Intensity at the end of | | | | | |
|---|---|---|---|---|---|---|---|---|
| | | | One minute | | 2 minutes | | 3 minutes | |
| | | | | | | | 15 | 7 |
| | 15 microosmoles of ADP | 7 microosmoles of ADP | 15 microosmoles | 7 microosmoles | 15 microosmoles | 7 microosmoles | microosmoles | microosmoles |
| Controls | 50.86 | 43.70 | 61.1 | 58.2 | 70.45 | 63.02 | 66.09 | 52.8 |
| Product according to the invention | 33.82 | 27.09 | 44.8 | 35.46 | 55.15 | 41.22 | 52.58 | 31.10 |
| Clofibrate | 40.42 | 35.58 | 51.14 | 43.05 | 59.07 | 47.54 | 55.33 | 33.47 |
| Moroxydine | 44.22 | 36.20 | 52.54 | 42.96 | 58.02 | 46.67 | 50.09 | 34.08 |

The products according to the invention have very interesting properties which appear to singularize them with respect to the effects of clofibrate and moroxydine alone.

The more distinct effects are the inhibition of platelet aggregation and the lowering of fibrinogen; these effects are to be found also both in the normolipidic rat and the hyperlipidic rat and in the rabbit (Although the best results are still those obtained with the stoichiometric product 1/1, in certain pathological cases it may be advantageous to have an unbalanced product).

TOXICITY

The intravenous LD50 (average 25 mice) is 380 mg/kg. The product is hence devoid of toxicity.

It is to be concluded from the foregoing description that whatever the type of application or administration, the derivatives of phenoxyisobutyric acids which are the subject of the present invention have with respect to previously known derivatives, numeorus advantages and notably those represented by a higher activity, the absence of side effects and the complete absence of toxicity and hypoglycemic effect.

As emerges from the foregoing, the invention is in no way limited to those of its types of application, embodiments, and uses which have just been described more explicitly; it encompasses, on the contrary, all modifications which may come to the spirit of the technician skilled in the art, without departing from the framework or the scope, of the present invention.

We claim:

1. Moroxydine phenoxyisobutyrates corresponding to the following general formula:

$$R-\phi-O-C(CH_3)_2-COO^{(-)} \quad (I)$$

$$O(CH_2CH_2)_2N-C(=NH)-NH-C(=NH)-NH_3^{\oplus}$$

in which R represents a chlorine atom or a $$R'-\phi-CO$$

group, R' being a chlorine atom.

2. Phenoxyisobutyrate according to claim 1, constituted by moroxydine clofibrate of formula I' below:

$$Cl-\phi-O-C(CH_3)_2-COO^{(-)} \quad (I')$$

$$O(CH_2CH_2)_2N-C(=NH)-NH-C(=NH)-NH_3^{\oplus}$$

3. Phenoxyisobutyrate according to claim 1, constituted by moroxydine, or 4-(4'-chloro-benxzoyl)-phenoxyisobutyrates of the following formula I'':

$$Cl-\phi-CO-\phi-O-C(CH_3)_2-COO^- \quad (I'')$$

$$O(CH_2CH_2)_2N-C(=NH)-NH-C(=NH)-NH_3^{\oplus}$$

4. Method of inhibiting platelet aggregation and lowering fibrinogen in mammals, comprising administering an efficient quantity of a moroxydine phenoxyisobutyrate according to claim 1, 2 or 3 to the animal.

* * * * *